(12) United States Patent
Parkins

(10) Patent No.: US 8,379,872 B2
(45) Date of Patent: Feb. 19, 2013

(54) TALK-THROUGH LISTENING DEVICE CHANNEL SWITCHING

(75) Inventor: John W. Parkins, Ithaca, NY (US)

(73) Assignee: Red Tail Hawk Corporation, Ithaca, NY (US)

( * ) Notice: Subject to any disclaimer, the term of this patent is extended or adjusted under 35 U.S.C. 154(b) by 275 days.

(21) Appl. No.: 12/785,767

(22) Filed: May 24, 2010

(65) Prior Publication Data

US 2011/0261965 A1 Oct. 27, 2011

Related U.S. Application Data

(60) Provisional application No. 61/182,921, filed on Jun. 1, 2009.

(51) Int. Cl.
*H04R 5/00* (2006.01)

(52) U.S. Cl. ............. 381/72; 381/71.67; 381/71.11; 381/71.14; 381/94.1; 381/94.7; 381/74; 381/322; 381/317; 381/367

(58) Field of Classification Search ............ 381/72, 381/71.6, 71.11, 71.14, 94.1, 94.7, 25, 74, 381/322, 317, 367
See application file for complete search history.

(56) References Cited

U.S. PATENT DOCUMENTS

| | | | | |
|---|---|---|---|---|
| 5,243,659 | A * | 9/1993 | Stafford et al. | 381/86 |
| 5,276,740 | A | 1/1994 | Inanaga et al. | |
| 6,118,878 | A | 9/2000 | Jones | |
| 6,975,731 | B1* | 12/2005 | Cohen et al. | 381/74 |
| 7,187,948 | B2* | 3/2007 | Alden | 455/557 |
| 8,189,827 | B2* | 5/2012 | Wedge | 381/310 |
| 2001/0046304 | A1 | 11/2001 | Rast | |
| 2004/0081323 | A1* | 4/2004 | Sung | 381/71.6 |
| 2004/0252852 | A1* | 12/2004 | Taenzer | 381/119 |
| 2005/0276421 | A1 | 12/2005 | Bergeron et al. | |
| 2006/0153394 | A1 | 7/2006 | Beasley | |
| 2006/0227976 | A1* | 10/2006 | Csermak et al. | 381/1 |
| 2007/0154027 | A1* | 7/2007 | Werner | 381/71.1 |
| 2007/0253569 | A1 | 11/2007 | Bose | |
| 2007/0274529 | A1* | 11/2007 | Nordin et al. | 381/72 |
| 2008/0199029 | A1* | 8/2008 | Loeppert | 381/309 |
| 2010/0119077 | A1* | 5/2010 | Platz et al. | 381/72 |
| 2012/0020491 | A1* | 1/2012 | Dory | 381/74 |

FOREIGN PATENT DOCUMENTS

GB 2431313 A 4/2007
JP H8-70493 A 3/1996

OTHER PUBLICATIONS

Targus Travel-Ease Active Noise Cancellation Headphones Review. Mar. 22, 2007 http://www.notebookreview.com/default.asp?newsID=3565&review=targus+noise+cancellation.
Sennheiser Electronic GmbH & Co. KG, Am Labor 1, 30900 Wedemark, Germany—Travel Line Headphones brochure—pages dealing with PXC450 model. Jan. 2007.
Napco International LLC—PICVC—Anr Helmet. 2004 http://www.napcointl.com/en/home/product_divisions/prod_desc/active_noise.html.

(Continued)

*Primary Examiner* — Davetta W Goins
*Assistant Examiner* — Kuassi Ganmavo
(74) *Attorney, Agent, or Firm* — Brown & Michaels, PC

(57) ABSTRACT

A talk-through system for hearing protectors such as headphones, helmets, earplugs and the like, in which separate left and right microphones are controlled by separate left and right switches. The microphones allow ambient sound to be heard by the wearer of the hearing protector, and normally the wearer hears audio from both microphones in the appropriate ears. Pushing a switch causes the audio from the ear on which the switch is mounted to be enhanced and, preferably, switched to both ears. Various arrangements of control logic are provided such that activation of a switch can cause changes in audio processing.

8 Claims, 2 Drawing Sheets

OTHER PUBLICATIONS

Racal Acoustics Talk-Through. Jul. 2008. http://www.racalacoustics.com/technology_innovation/situational_awareness/talk-through.aspx.

Racal Acoustics Ltd., Waverley Industrial Park, Halsham Drive, Harrow, Middlesex, England HA1 4TR-RA108 Slimgard II Headset brochure. Jun. 2006.

Racal Acoustics Ltd., Waverley Industrial Park, Halsham Drive, Harrow, Middlesex, England HA1 4TR-RA5000 Raptor Headset brochure. Jan. 2007.

Associated Industries—DH-132S and DH-132AS CVC Helmets. 2007 http://www.associated-ind.com/vehicular_products_dh132s.htm.

Weatherless, et al. "Effects of the Advanced Combat Helmet (ACH) and Selected Communications and Hearing Protection Systems (C&HPSs) on Speech Communication: Talk-Through Systems" Army Research Laboratory ARL-TR-4078—Apr. 2007.

* cited by examiner

TALK-THROUGH LISTENING DEVICE CHANNEL SWITCHING

REFERENCE TO RELATED APPLICATIONS

This application claims one or more inventions which were disclosed in Provisional Application No. 61/182,921, filed Jun. 1, 2009, entitled "Talk-Through Listening Device Channel Switching". The benefit under 35 USC §119(e) of the United States provisional application is hereby claimed, and the aforementioned application is hereby incorporated herein by reference.

ACKNOWLEDGMENT OF GOVERNMENT SUPPORT

This invention was made with Government support under SBIR Phase II contract N68335-06-C-0372, awarded by the US Navy. The government has certain rights in the invention.

BACKGROUND OF THE INVENTION

1. Field of the Invention

The invention pertains to the field of hearing protection. More particularly, the invention pertains to hearing protectors having talk-through capability.

2. Description of Related Art

Talk-through listening systems typically comprise hearing protection devices (i.e. earplugs, headsets, helmets) with microphones mounted on their outside surface. The microphones convert sound pressure levels (SPLs) to an electrical signal. The electrical signals are amplified and used to drive audio transducers such as speakers in headphones, helmets, or earplugs or the like. Electronic automatic gain control and limiting devices ensure that the SPL generated in the canals of the user are kept within safe levels. In this way, the user can monitor sound in a high-SPL environment at safe SPLs.

One example of such an environment is the flight deck of aircraft carriers. Aircraft maintainers need to service aircraft under extremely high noise conditions. However, they need to be aware of their surroundings and must communicate to each other. The maintainers must know if a vehicle or plane is approaching from areas outside of their view. For this, they use acoustic cues. Moreover, the maintainers often need to communicate with each other face-to-face in high acoustic noise, without the use of radios.

SUMMARY OF THE INVENTION

The invention presents a talk-through system for hearing protectors such as headphones, helmets, earplugs and the like, in which separate left and right microphones are controlled by separate left and right switches. The microphones allow ambient sound to be heard by the wearer of the hearing protector, and normally the wearer hears audio from both microphones in the appropriate ears. Pushing a switch causes the audio from the ear on which the switch is mounted to be enhanced and, preferably, switched to both ears. Various arrangements of control logic are provided such that activation of a switch can cause changes in audio processing.

DETAILED DESCRIPTION OF THE INVENTION

The system of the invention can provide a means to improve face-to-face speech communications of individuals using talk-through systems.

Figure 1:
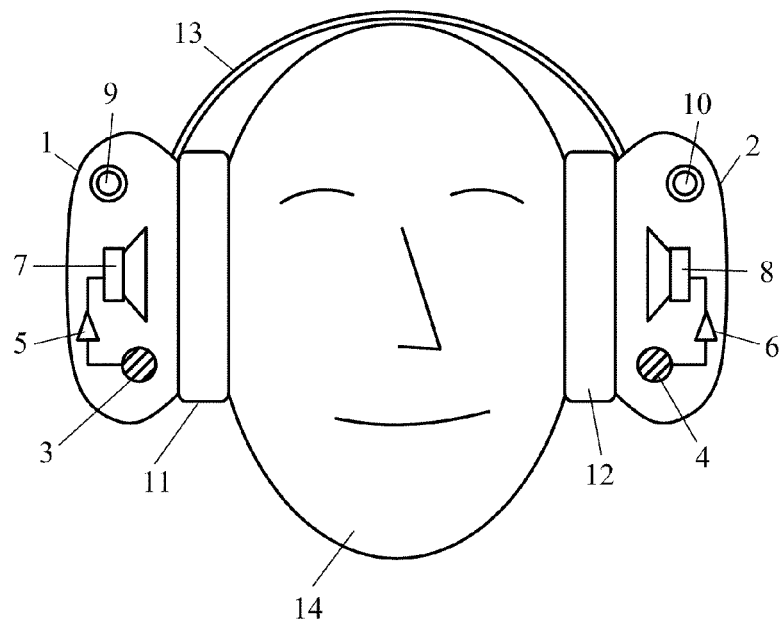
FIG. 1 shows a diagram of a talk-through headphone system

A drawing of a talk-through headset system useful with the system of the invention is shown in diagrammatic form in FIG. 1. A hearing protection device, shown as headset 13, has a right ear protector (earcup 1) and a left protector (earcup 2) to reduce the amount of outside noise entering the ears of the user 14. The earcups 1 and 2 have microphones 3 and 4, respectively, which are directed to pick up sounds outside of the earcups. Each microphone signal is amplified and processed by a processor circuit 5 and 6 and this signal is input to speakers 7 and 8, one in each of earcups 1 and 2.

The microphone signal can be fed to the user via a speaker located within the earcup, as shown in FIG. 1, or within an earplug under the earcup. In this way, natural hearing is restored to the user. Electronic circuits can be used to automatically adjust the gain of the ambient noise signal which turn down the volume automatically in high noise environments and/or compress the signal to prevent hearing damage. A volume control can be provided to vary the volume of the ambient signal to comfortable levels.

The switching system can be used on helmets, headsets, and in-ear communications devices as well as other devices.

Switches 9 and 10 are used to control the switching and speech-enhancing circuitry, enabling the user to hear acoustic speech communications more clearly. Switches 9 and 10 are preferably pushbuttons, but it will be understood that other kinds of switches could be substituted within the teachings of the invention.

It is advantageous to have the switches 9 and 10 located generally behind the earcups 1 and 2. When the user 14 uses his/her thumb to press the switch 9 or 10, he/she forms a "cup shape" around the microphone. This "cupping" is often used by persons in everyday life not using any headgear when they wish to hear speech better. The cupping shields sounds from the rear and amplifies sounds from the front. In addition, the cupping amplifies sounds in the speech frequency band.

Locating the switches in this way results in improved speech intelligibility when the speech is hard to hear and/or there is significant background noise and also results in an intuitive procedure. Alternatively, the switches 9 and 10 can be mounted elsewhere on the hearing protector, or on helmets, earplug earshells, cables, or on a separate control box or other position as may be desired.

Figure 2:
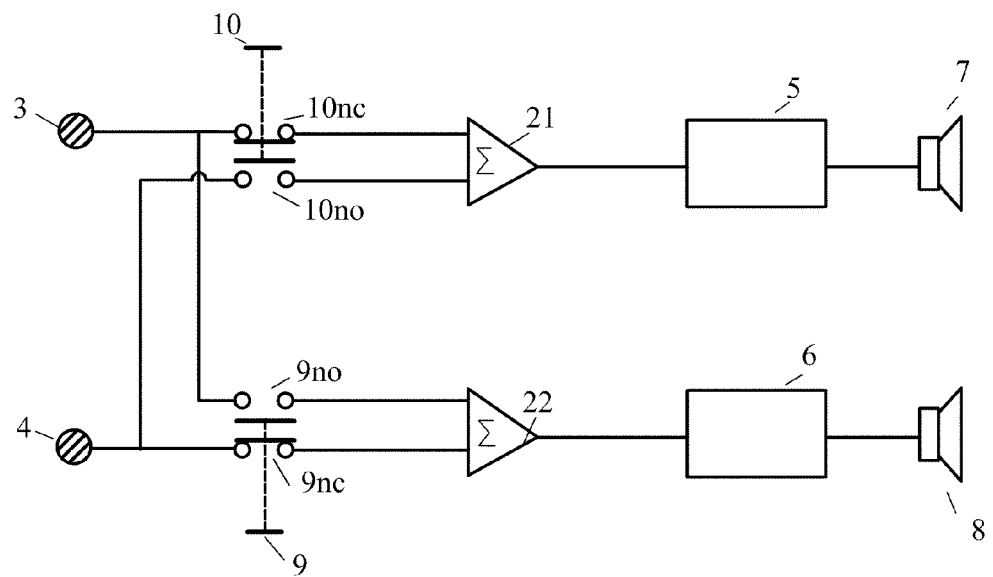
FIG. 2 shows a block diagram of one embodiment of the invention

Referring to the embodiment shown in FIG. 2, switch 9 on the right side 1 has two ganged sets of contacts—contacts 9no are normally open, and contacts 9nc are normally closed. Similarly, switch 10 on the left side 2 has normally open contacts 10no and normally closed contacts 10nc.

Audio signals from right-side microphone 3 pass through normally-closed contacts 10nc of left hand switch 10 into one input of summing amplifier 21. The output of the summing amplifier 21 is further amplified and, optionally filtered or otherwise processed in processor 5, and the amplified signal is fed to right speaker 7. The left side 3 operates similarly—audio signals from left-side microphone 4 pass through normally-closed contacts 9nc of right hand switch 9 into one input of summing amplifier 22. The output of the summing amplifier 22 is further amplified and, optionally filtered or otherwise processed in processor 6, and the amplified signal is fed to left speaker 8. The audio signals from right-side microphone 3 are also connected to the normally open contacts 9no of right hand switch 9, and the audio signals from left-side microphone 4 are also connected to normally open contacts 10no of left hand switch 10.

Thus, under normal operation, the earcups 1 and 2 block most of the ambient acoustic noise from the surroundings. With neither left switch 10 nor right switch 9 pressed, the microphones 3 and 4 pick up ambient sounds which, routed through the normally closed contacts 10nc and 9nc to summing amplifiers 21 and 22 and processors 5 and 6, are heard by the user 14 in speakers 7 and 8, respectively.

During face-to-face communications the user 14 may opt to push the left switch 10 or right switch 9, depending on which side the person talking to them is standing, or on which side a sound the user wants to hear is coming from. When the user pushes left hand switch 10, the normally open contacts 10no are closed routing the signal from left microphone 4 to summing amplifier 21, and the normally closed contacts 10nc are opened, breaking the connection between right microphone 3 and summing amplifier 21. In this way, the signal from the left microphone 4 is used to drive both left speaker 8 and right speaker 7, and the right microphone 3 is out of the circuit. The communicator can talk directly into the left microphone 4 in close proximity which increases the speech-to-noise signal ratio.

Similarly, if the user 14 opts to push the right hand switch 9, the normally open contacts 9no are closed routing the signal from right microphone 3 to summing amplifier 22, and the normally closed contacts 9nc are opened, breaking the connection between left microphone 4 and summing amplifier 22. In this way, the signal from the right microphone 3 is used to drive both left speaker 8 and right speaker 7, and the left microphone 4 is out of the circuit.

The switching logic in the example of this FIG. 2 may be summarized in the following table 1:

TABLE 1

| | Switch Logic in FIG. 2 | | |
|---|---|---|---|
| Switch Contact | Neither 9 (R) nor 10 (L) is operated | 9 (R) Operated | 10 (L) Operated |
| 9nc | Closed | Open | Closed |
| 9no | Open | Closed | Open |
| 10nc | Closed | Closed | Open |
| 10no | Open | Open | Closed |

It will be understood by one skilled in the art that the blocks in the block diagrams allow for variations and additions within the teachings of the invention. The amplifiers may be of any sort known in the art, the processors may include filtering, digital or analog audio shaping and other processing circuits as well as additional amplifiers or attenuators or controls, and the speakers may include audio transducers of any kind known to the art. The switches 9 and 10, while drawn as simple multi-pole mechanical switches, may be implemented as fully solid-state circuits with touch actuators of any convenient sort.

Figure 3:
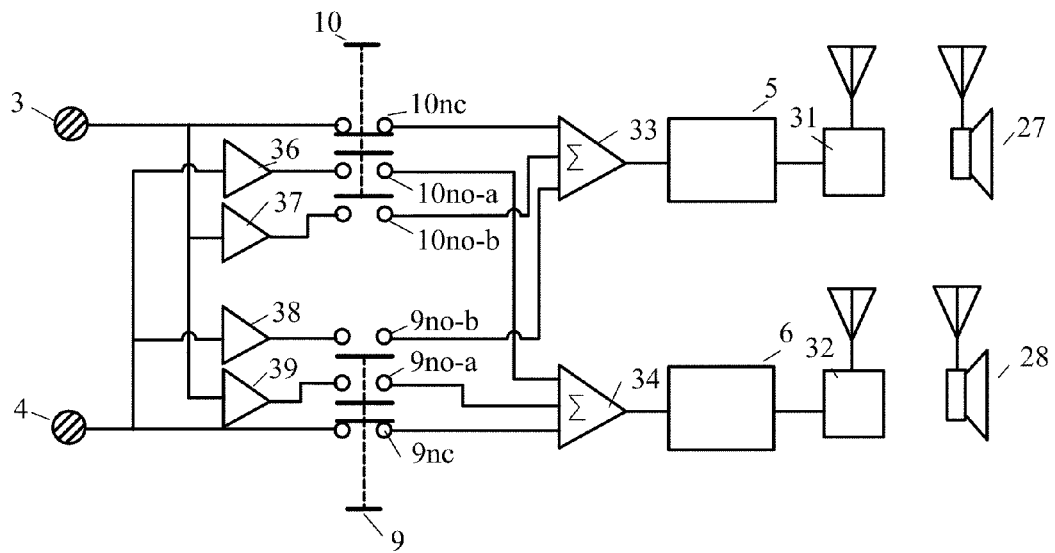
FIG. 3 shows a block diagram of an alternative embodiment of the invention

FIG. 3 shows an alternative embodiment of the switching system. In this embodiment, instead of completely muting the unselected microphone as described above, an attenuated signal from that microphone is still heard. To accomplish this, a second set of normally open contacts is added to each switch 9 and 10, and a set of attenuators 36, 37, 38 and 39 are used. Attenuators 37 and 38 preferably have an attenuation of at least 6 dB, while attenuators 36 and 39 preferably have an attenuation between 0 dB and 6 dB. Left-side attenuators 36 and 38 have inputs coupled to left microphone 4, with the output of attenuator 36 coupled to normally open contact 10no-a of left switch 10 and the output of attenuator 38 coupled to normally open contact 9no-b of right switch 9. Right-side attenuators 37 and 39 have inputs coupled to right microphone 3, with the output of attenuator 37 coupled to normally open contact 10no-b of left switch 10, and the output of attenuator 39 coupled to normally open contact 9no-a of right switch 9. The switching logic can thus be summarized in table 2, below:

TABLE 2

| | Switch Logic in FIG. 3 | | |
|---|---|---|---|
| Switch Contact | Neither 9 (R) nor 10 (L) is operated | 9 (R) Operated | 10 (L) Operated |
| 9nc | Closed | Open | Closed |
| 9no-a | Open | Closed | Open |
| 9no-b | Open | Closed | Open |
| 10nc | Closed | Closed | Open |
| 10no-a | Open | Open | Closed |
| 10no-b | Open | Open | Closed |

In the example shown in this FIG. 3, the output of processors 5 and 6 is sent to wireless transmitters 31 and 32 instead of speakers. Sometimes in very noisy environments, both earplugs and earcups are worn. The wireless transmitters 31 and 32 would transmit their signals to wireless earplugs 27 and 28 used by the user. Alternatively, the signals could be sent via wires to earplugs with speakers in them.

In this embodiment, under normal operation when neither right switch 9 nor left switch 10 is operated, normally closed contacts 9nc and 10nc are closed and the system operates in stereo. That is, the audio output of right microphone 3 is coupled through normally closed contacts 10nc to an input of summing amplifier 33, the output of which is coupled to processor 5, and the processed output is sent to wireless transmitter 31. Similarly, the audio output of left microphone 4 is coupled through normally closed contacts 9nc to an input of summing amplifier 34, then to processor 6 and to wireless transmitter 32.

When the left switch 10 is pressed, the left microphone 4 remains connected through normally closed contacts 9nc of the right switch 9 to an input of summing amplifier 34, then to processor 6 and to wireless transmitter 32. The normally closed contacts 10nc open, disconnecting the full output of right microphone 3 from summing amplifier 33. Normally open contacts 10no-a and 10no-b close, which causes the attenuated signal from the right microphone 3—that is, the output of attenuator 37—and an attenuated signal from left microphone 4—that is, the output of attenuator 36—to be combined in summing amplifier 33. The combined attenuated signals are then coupled to processor 5 and output to transmitter 31. Thus, the full audio from the left microphone 4 appears on the left earphone 28 (received from left transmitter 32), and the right earphone 27 (received from right transmitter 31) receives a mixture of attenuated signals from both the right microphone 3 and the left microphone 4.

The operation when the right switch 9 is pressed is the reverse of that described above. The right microphone 3 remains connected through normally closed contacts 10nc of the left switch 10 to an input of summing amplifier 33, then to processor 5 and to wireless transmitter 31. The normally closed contacts 9*nc* open, disconnecting the full output of left microphone 4 from summing amplifier 34. Normally open contacts 9*no-a* and 9*no-b* close, which causes the attenuated signal from the left microphone 4—that is, the output of attenuator 38—and an attenuated signal from right microphone 3—that is, the output of attenuator 39—to be combined in summing amplifier 34. The combined attenuated signals are then coupled to processor 6 and output to transmitter 32. Thus, the full audio from the right microphone 3 appears on the right earphone 27 (received from right transmitter 31), and the left earphone 28 (received from left transmitter 32) receives a mixture of attenuated signals from both the right microphone 3 and the left microphone 4.

The arrangement of FIG. 3 allows the user to maintain acoustic directional cues, by retaining some of the unselected audio in the unselected ear.

Figure 4:
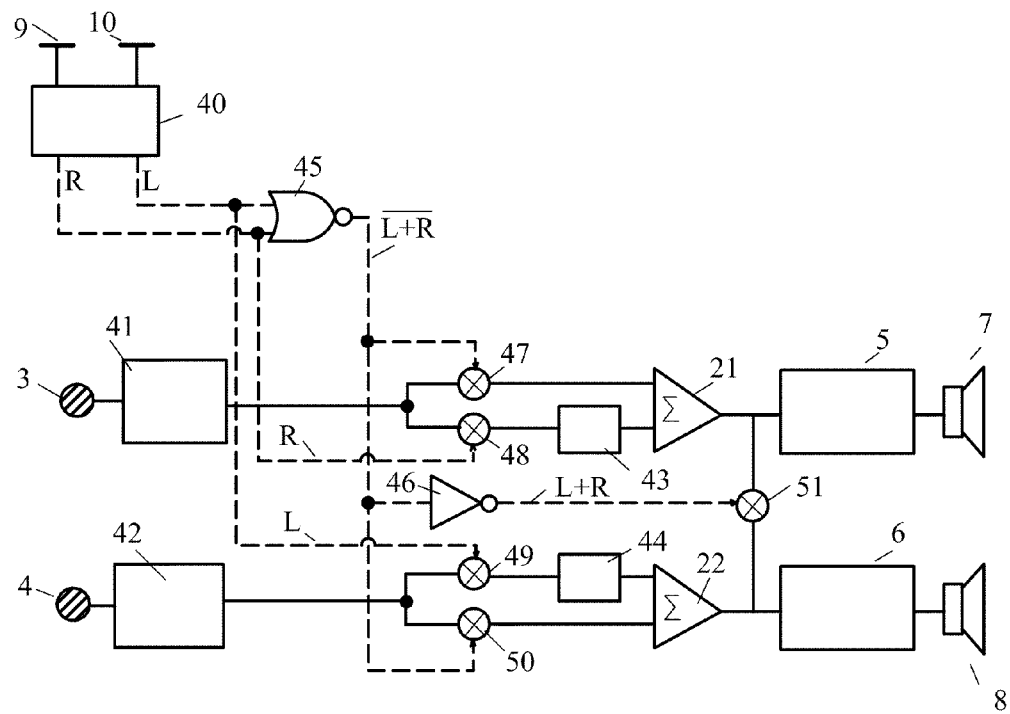
FIG. 4 shows a block diagram of another alternative embodiment of the invention

In another embodiment of the invention, shown in FIG. 4, when switch 9 or 10 is pressed, not only does the channel switching occur, but the signal is processed for better speech intelligibility. In this example, electronic switching is shown rather than the multi-contact switches shown in the previous examples. The right switch 9 and left switch 10 activate electronics in logic module 40 which converts the key presses into outputs R and L (for right and left switch operation, respectively) with the proper logic levels for the switching circuitry.

The audio from right microphone 3 is optionally routed through pre-processing circuitry 41 to switches 47 and 48. The output of switch 47 is fed to an input of summing amplifier 21, and the output of switch 48 is processed in right speech enhancing circuit 43, and then fed to another input of summing amplifier 21. As in the embodiment of FIG. 1, the output of summing amplifier 21 is further amplified and, optionally filtered or otherwise processed in processor 5, and the amplified signal is fed to right speaker 7. The left side operates similarly—audio signals from left-side microphone 4 are optionally routed through pre-processing circuitry 42 to switches 49 and 50. The output of switch 50 is fed to an input of summing amplifier 22, and the output of switch 49 is processed in left speech enhancing circuit 44, and then fed to another input of summing amplifier 22. As in the embodiment of FIG. 1, the output of summing amplifier 22 is further amplified and, optionally filtered or otherwise processed in processor 6, and the amplified signal is fed to left speaker 8. Switch 51 acts to combine the outputs of summing amplifiers 21 and 22, so that when switch 51 is closed both processors 5 and 6 are fed with the same audio signal.

Pre-processing electronics blocks 41 and 42 account for any equalization and compression that may be used as well as other processing electronics commonly used in audio systems.

The speech-enhancement circuitry 43 and 44 can be something as simple as speechband filters—that is, a high-pass filter combined with a low-pass filter designed to pass frequencies within the speech band while attenuating frequencies outside of the speech band. The speech-enhancement circuitry could employ other speech-enhancement techniques as well.

The switches 47, 48, 49, 50 and 51 are operated by the L and R signals from logic circuit 40, in combination with NOR gate 45 and inverter 46. Specifically, the inputs to NOR gate 45 are L and R, and the output is NOT (L OR R)—that is, the output of the NOR gate is active when neither L nor R is active (i.e. neither switch is operated). The output of NOR gate 45 operates switches 47 and 50, and is input to inverter 46. The output of inverter 46 is the inverse of the output of NOR gate 45—that is, it is active when either L or R is active (i.e. either switch is operated)—and operates switch 51. Switch 48 is operated by R (i.e. closed when right switch 9 is operated), and switch 49 is operated by L (i.e. closed when left switch 10 is operated). This can be summarized in the following table 3:

TABLE 3

Switch Logic in FIG. 4

| Switch | Neither 9 (R) nor 10 (L) is operated | 9 (R) Operated | 10 (L) Operated |
|---|---|---|---|
| 47 | Closed | Open | Open |
| 48 | Open | Closed | Open |
| 49 | Open | Open | Closed |
| 50 | Closed | Open | Open |
| 51 | Open | Closed | Closed |

In this embodiment, under normal operation when neither right switch 9 nor left switch 10 is operated, switches 47 and 50 are closed and the system operates in stereo. That is, the audio output of right microphone 3 is coupled through switch 47 to an input of summing amplifier 21, the output of which is coupled to processor 5, and the processed output is sent to speaker 7. Similarly, the audio output of left microphone 4 is coupled through switch 50 to an input of summing amplifier 22, then to processor 6 and to speaker 8.

When the left switch 10 is pressed, L is active, closing switch 49 and causing the output of NOR gate 45 to be inactive, which opens switches 47 and 50 and closes switch 51. The left microphone 4 is thus connected through switch 49 to left speech-enhancement circuitry 44, and, with switches 48 and 50 open, the right microphone 3 is disconnected from summing amplifier 21. Switch 51 connect the outputs of summing amplifiers 21 and 22 together, so that the signal from the left microphone 4 is routed to both the left 6 and right 5 processors and left 8 and right 7 speakers.

The operation when the right switch 9 is pressed is the reverse of that described above—R is active, closing switch 48 and causing the output of NOR gate 45 to be inactive, which opens switches 47 and 50 and closes switch 51. The right microphone 3 is thus connected through switch 48 to right speech-enhancement circuitry 43, and, with switches 49 and 50 open, the left microphone 3 is disconnected from summing amplifier 22. Switch 51 connect the outputs of summing amplifiers 21 and 22 together, so that the signal from the right microphone 3 is routed to both the left 6 and right 5 processors and left 8 and right 7 speakers.

The switching system can be used on helmets, headsets, and in-ear communications devices as well as other devices. As noted above, the left 10 and right 9 switches can be located on the earcups, helmets, earplug earshells, cables, or an electronics box worn on a belt among other locations.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A talk-through listening system comprising:
   a) a hearing protection device comprising:
      i) a left ear protector comprising:
         A) a left protector for reducing outside noise entering a user's left ear;
         B) a left audio transducer having a signal input and an audio output for coupling audio signals to the user's left ear; and C) a left microphone on an outside of the left protector for picking up sound outside the ear protector, having an output;
ii) a right ear protector comprising:
A) a right protector for reducing outside noise entering a user's right ear;
B) a right audio transducer having a signal input and an audio output for coupling audio signals to the user's right ear; and
C) a right microphone on an outside of the right protector for picking up sound outside the ear protector, having an output;
b) a right switch for controlling switching operation;
c) a left switch for controlling switching operation;
d) talk-through switching coupled to the output of the left microphone and the output of the right microphone and the left audio transducer and the right audio transducer and the left switch and the right switch;
the talk-through switching being arranged such that when the left switch is operated the output of the left microphone is coupled to the signal input of the left audio transducer and the signal input of the right audio transducer, and when the right switch is operated the output of the right microphone is coupled to the signal input of the left audio transducer and the signal input of the right audio transducer.

2. The talk-through system of claim 1, in which the left audio transducer and the right audio transducer each comprise an amplifier and a speaker.

3. The talk-through system of claim 1, in which the left audio transducer and the right audio transducer each comprise a wireless transmitter coupled to a wireless earplug.

4. The talk-through system of claim 1, in which, when either the left switch is operated or the right switch is operated, an attenuated signal from the opposite microphone is also coupled to the signal input of the left audio transducer and the signal input of the right audio transducer.

5. The talk-through system of claim 1, in which each of the left ear protector and the right ear protector further comprises a speech enhancing circuit coupled to the talk-through switching, such that when the left switch is operated the output of the left microphone is processed by the speech enhancing circuit of the left ear protector, and when the right switch is operated the output of the right microphone is processed by the speech enhancing circuit of the right ear protector.

6. The talk-through system of claim 5, in which the speech enhancing circuit comprises a speech band filter.

7. The talk-through system of claim 1 in which each of the left microphone and the right microphone further comprises a pre-processing circuit.

8. The talk-through system of claim 1, in which each of the left switch and the right switch are mounted at a rear of the ear protector, such that a user can activate the switch while cupping a hand around the microphone.

* * * * *